United States Patent
Schiendzielorz et al.

(10) Patent No.: US 10,485,925 B2
(45) Date of Patent: Nov. 26, 2019

(54) MEDICAMENT DELIVERY DEVICE WITH ROTATABLE HOUSING ON A BASE

(71) Applicant: Sanofi, Paris (FR)

(72) Inventors: Eva Schiendzielorz, Frankfurt am Main (DE); Stefan Wendland, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/510,400

(22) PCT Filed: Sep. 11, 2015

(86) PCT No.: PCT/EP2015/070868
§ 371 (c)(1),
(2) Date: Mar. 10, 2017

(87) PCT Pub. No.: WO2016/041870
PCT Pub. Date: Mar. 24, 2016

(65) Prior Publication Data
US 2017/0281861 A1    Oct. 5, 2017

(30) Foreign Application Priority Data
Sep. 15, 2014    (EP) .................................... 14306418

(51) Int. Cl.
*A61M 5/14*    (2006.01)
*A61M 5/142*    (2006.01)
(Continued)

(52) U.S. Cl.
CPC ...... *A61M 5/14248* (2013.01); *A61M 5/1452* (2013.01); *A61M 5/158* (2013.01);
(Continued)

(58) Field of Classification Search
CPC .... A61M 5/14248; A61M 2005/14282; A61M 2005/14256; A61M 2005/1426
See application file for complete search history.

(56) References Cited

U.S. PATENT DOCUMENTS 5,814,020 A    9/1998   Gross
6,979,316 B1 *  12/2005  Rubin ................. A61M 5/2033
                                                   604/131
(Continued)

FOREIGN PATENT DOCUMENTS

CN    1671430     9/2005
CN    101772359   7/2010
(Continued)

OTHER PUBLICATIONS

International Search Report and Written Opinion in International Application No. PCT/EP2015/070868, dated Dec. 10, 2015, 12 pages.
(Continued)

*Primary Examiner* — William R Carpenter
(74) *Attorney, Agent, or Firm* — Fish & Richardson P.C.

(57) ABSTRACT

A medicament delivery device (10) comprises a medicament delivery mechanism including an injection needle (23). A housing (11) contains at least one component of the medicament delivery mechanism. A base plate (12) includes a contact surface (12b) for placement against a patient's body. The housing (11) is moveably connected to the base plate (12) and is moveable relative to the base plate (12) between a first position and a second position. The medicament delivery mechanism is operative upon movement of the housing (11) from the first position to the second position.

14 Claims, 6 Drawing Sheets

(51) Int. Cl.
    *A61M 5/145*    (2006.01)
    *A61M 5/158*    (2006.01)
    *A61M 5/168*    (2006.01)
(52) U.S. Cl.
    CPC . *A61M 5/1684* (2013.01); *A61M 2005/14256* (2013.01); *A61M 2005/1585* (2013.01); *A61M 2205/581* (2013.01); *A61M 2205/583* (2013.01)

(56) References Cited

U.S. PATENT DOCUMENTS

| | | | | |
|---|---|---|---|---|
| 2003/0083645 | A1* | 5/2003 | Angel | A61M 5/14248 604/890.1 |
| 2004/0116865 | A1 | 6/2004 | Bengtsson | |
| 2013/0046239 | A1* | 2/2013 | Gonnelli | A61M 5/14248 604/135 |
| 2016/0354553 | A1* | 12/2016 | Anderson | A61M 5/3298 |

FOREIGN PATENT DOCUMENTS

| | | |
|---|---|---|
| JP | H11-313889 | 11/1999 |
| JP | 2005-525141 | 8/2005 |
| JP | 2006-501893 | 1/2006 |
| WO | WO 97/21457 | 6/1997 |
| WO | WO 03/037403 | 5/2003 |
| WO | WO 2004/030726 | 4/2004 |
| WO | WO 2005/018703 | 3/2005 |
| WO | WO 2011/075105 | 6/2011 |
| WO | WO 2013/032841 | 3/2013 |
| WO | WO-2014086684 A1 * 6/2014 ............ A61M 5/002 |  |

OTHER PUBLICATIONS

International Preliminary Report on Patentability in International Application No. PCT/EP2015/070868, dated Mar. 21, 2017, 8 pages.

* cited by examiner

MEDICAMENT DELIVERY DEVICE WITH ROTATABLE HOUSING ON A BASE

CROSS-REFERENCE TO RELATED APPLICATIONS

This application is a U.S. national stage application under 35 USC § 371 of International Application No. PCT/EP2015/070868, filed on Sep. 11, 2015, which claims priority to European Patent Application No. 14306418.6 filed on Sep. 15, 2014, the entire contents of which are incorporated herein by reference.

TECHNICAL FIELD

The present disclosure relates to a device for delivery of medicament to a patient.

BACKGROUND

A variety of diseases exist that require regular treatment by injection of a medicament. Such injections can be performed by using injection devices. Various injection pumps for delivering bolus injections are known in the art. Generally such devices are operated by the patient's themselves, although they may also be operated by medical personnel.

To use an injection pump, it is first supported on a suitable injection site on a patient's skin and, once installed, injection is initiated by the user. Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. Large volume devices ("LVDs") for administering such biological medicaments may comprise a pre-filled disposable drug delivery device or, alternatively, a disposable drug delivery device into which a patient or medical personnel must insert a drug cartridge prior to use.

There are typically a number of steps that need to be performed for use of injection devices by the user before medicament injection can begin. Whilst handling the device in the pre-injection phase of operation it is possible that the user may accidentally initiate the injection and then medicament delivery. This can occur either when the patch pump is not installed on the user at all or when the device is only partly installed and is not secured at the correct location on the user. Such errors are at best inconvenient and at worst can present safety issues.

SUMMARY

In certain aspects, a medicament delivery device which can mitigate the risk of accidental triggering of the operation of the device is provided.

In some aspects, a medicament delivery device is provided. The medicament delivery device includes a medicament delivery mechanism including an injection needle, a housing containing at least one component of the medicament delivery mechanism, a base plate with a contact surface for placement against a patient's body, wherein the housing is moveably connected to the base plate and is moveable relative to the base plate between a first position and a second position, and wherein the medicament delivery mechanism is operative upon movement of the housing from the first position to the second position. The device may thereby advantageously require movement of housing to enable medicament delivery, and may thereby mitigate the risk of accidental operation of the device.

The base plate may include an aperture through which the needle is able to extend. This may advantageously provide protection for the needle by the needle being surrounded by the base plate in operative position.

Movement of the housing from the first position to the second may comprise moving the injection needle from a position in which it is blocked by the base plate to a position in which it points to the aperture to enable it to extend therethrough to inject a patient. This may advantageously prevent a user accessing the needle until the device is intended to be used, and may also prevent accidental movement of the needle to project from the housing until the housing is moved into the second position.

The injection needle may be mounted to the housing and may be moved into alignment with the aperture in the base plate when the housing is moved into the second position. This may advantageously only enable the needle to pierce the skin in the second position of the device, providing a safety feature.

The housing may include a needle aperture through which the needle is able to extend, and the needle aperture and the aperture in the base plate may be aligned when the housing is in the second position and may be out of alignment with the housing is in the first position.

The medicament delivery mechanism may be configured to automatically initiate a medicament delivery process when the housing is moved into the second position. This may advantageously reduce necessary patient interaction with the device in use, and thereby simplify operation.

The medicament delivery mechanism may be activated when the housing is moved into the second position and the medicament delivery device may include a manually-operable actuator for a patient to initiate a medicament delivery process once the housing is moved into the second position. This may advantageously provide an additional safety feature to further mitigate against accidental operation of the device.

The needle may be moveable between an engaged position in which it projects outwardly beyond the contact surface of the base plate, and a retracted position. This may advantageously mitigate against patient interaction with the needle until the device is ready for a medicament delivery process to commence.

The medicament delivery mechanism may comprise a needle insertion mechanism which is configured such that the needle is automatically moved into the engaged position as the housing is moved into the second position. This may advantageously reduce the number of actions a patient needs to make in use of the device. Also, this may further prevent accidental exposure of the needle until a medicament delivery process is to be commenced. The needle insertion mechanism may comprise mechanically cooperating elements which move the needle into the engaged position. Such mechanical elements may include a cam surface and a cooperating cam follower. Alternatively, the needle insertion mechanism may be electrically powered and actuated upon detection of the housing moving into the second position. Such detection may be by electrical contacts or other sensor means.

The medicament delivery device may further comprise a biasing element configured to urge the housing into the first position. This may advantageously give resistance to movement to the second position, giving the device an improved tactile quality. This may also allow for an auto-return feature of the housing to the first position.

The medicament delivery mechanism may be at least partially powered by a medicament delivery mechanism driver, and moving the housing into the second position may energize the medicament delivery mechanism driver. This may advantageously enable a significant amount of energy or force to be provided to the medicament delivery device driver from user-applied work.

The medicament delivery mechanism may comprise a controller and the movement of the needle and/or the medicament delivery process may be controlled by the controller.

The medicament delivery device may comprise a locking mechanism configured to lock the housing in the second position relative to the base plate. This may advantageously secure the device in operative position and may mitigate the likelihood of accidental movement to the first position during use.

The medicament delivery mechanism may be configured to automatically release the locking mechanism upon completion of a medicament delivery process. The locking mechanism may be electronically controlled. The locking mechanism may comprise cooperating mechanical locking elements, such as latch members. The unlocking may be effected upon detection of a medicament driver or plunger reaching a position signifying an end to a medicament delivery process. The locking mechanism may include a solenoid to move a locking element out of engagement to release the locking mechanism. This may advantageously provide improved patient usability, by reducing patient interaction with the device during a medicament delivery process, and also may provide an indicator of the end of a medicament delivery process.

The housing may be rotatably connected to the base plate so as to be rotatable relative to the base plate between the first and second positions. This may advantageously provide an ergonomic configuration of movement of the device in a compact device configuration.

The housing may be connected to the base plate so as to be rotatable about an axis substantially perpendicular to the plane of the base plate. This may advantageously enable enhanced usability for a patient by providing a bio-mechanically convenient activation movement of the device. Also, this configuration may advantageously be such that the movement of the housing relative to the base plate to activate the device is a different movement or motion to that required to secure the device to the patient's body. This may help towards preventing accidental triggering of the device.

The housing may be rotatable about a limited range of rotation relative to the base plate and the first and second positions may be respectively disposed proximate extremes of the range of movement. This may advantageously help define the respective positions of the housing relative to the base plate and help ensure the housing is moved into the respective positions.

The housing and the base plate may be re coupled by a rotational mechanism configured such that after a medicament delivery process is initiated once the housing has been rotated into the second position, the housing rotates back to the first position during the period of the medicament delivery process. This may advantageously provide an indicator to the patient as to the progress of the medicament delivery process.

The needle and/or a needle insertion mechanism may be mounted to the base plate.

The housing may be moveable relative to the base plate beyond the second position from the first position, and moveable back to the second position for operation of the medicament delivery mechanism. This may advantageously allow for over-movement, including over-rotation, of the housing relative to the base plate. This may also advantageously avoid the need for a patient to accurately locate the housing in the second position and the housing may be ensure housing reaches the second position by moving beyond the second position and then back to the second position. The housing may be moveable beyond the second position by a predetermined degree or distance and movement beyond the predetermined degrees or distance may be prevented. Engaging elements on the housing and base plate may define the predetermined degree or distance, and may defined the predetermined degree or distance by coming into abutment at the predetermined degree or distance.

The medicament delivery device may be fitted with a container of medicament.

In certain aspects, a method of operating a medicament delivery device having a medicament delivery mechanism is provided. The medicament delivery device includes an injection needle, a housing containing at least one component of the medicament delivery mechanism, and a base plate with a contact surface for placement against a patient's body, the housing being moveably connected to the base plate and moveable relative to the base plate between a first position and a second position, the method comprising rendering the medicament delivery mechanism operative upon movement of the housing from the first position to the second position.

BRIEF DESCRIPTION OF THE DRAWINGS

Embodiments will now be described, by way of example only, with reference to the accompanying drawings, in which.

DETAILED DESCRIPTION

Figure 1:
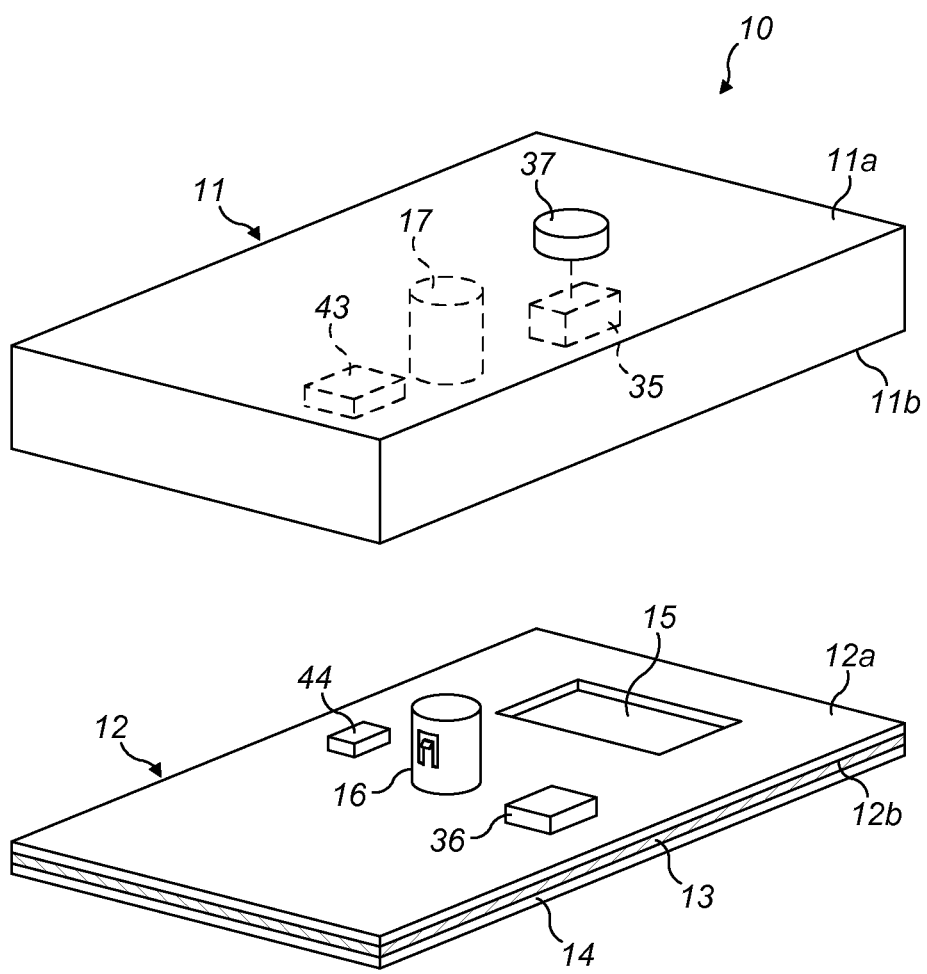
FIG. 1 shows an exploded perspective view of a medicament delivery device of a first embodiment.

FIGS. 1 to 4 show a medicament delivery device 10, which in the exemplary embodiment comprises a bolus injector device (hereafter simply referred to as "device 10"), according to a first embodiment. Device 10 can comprise a housing 11 defining an interior cavity containing various components of a medicament delivery system, and a base plate 12 upon which the housing 11 is moveably mounted so that the housing 11 can rotate relative to the base plate 12. One type of device 10 includes an LVD.

The base plate 12 is a substantially planar component having an upper surface 12a and a lower surface 12b. In use of the device 10, the lower surface 12b is to be placed against a patient's skin and includes a layer of adhesive 13 to secure the device 10 in place on the patient during a medicament delivery process. A removable cover sheet 14 is provided over the top of the layer of adhesive 13 which is peeled off the lower surface 12b of the base plate 12 immediately prior to applying the device 10 to the patient's skin.

The base plate 12 includes an aperture 15 to allow access to the patient's skin through the base plate 12 when the base plate 12 is adhered to a patient's skin. A post 16 extends perpendicularly from the upper surface 12a of the base plate 12.

Figure 2:
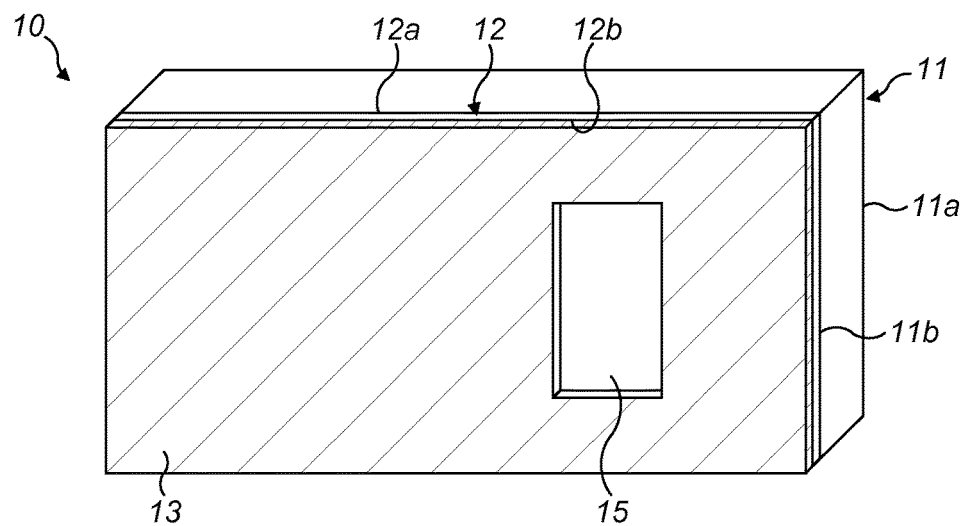
FIG. 2 shows a plan view from below of the medicament delivery device of FIG. 1 in a first position.
Figure 3:
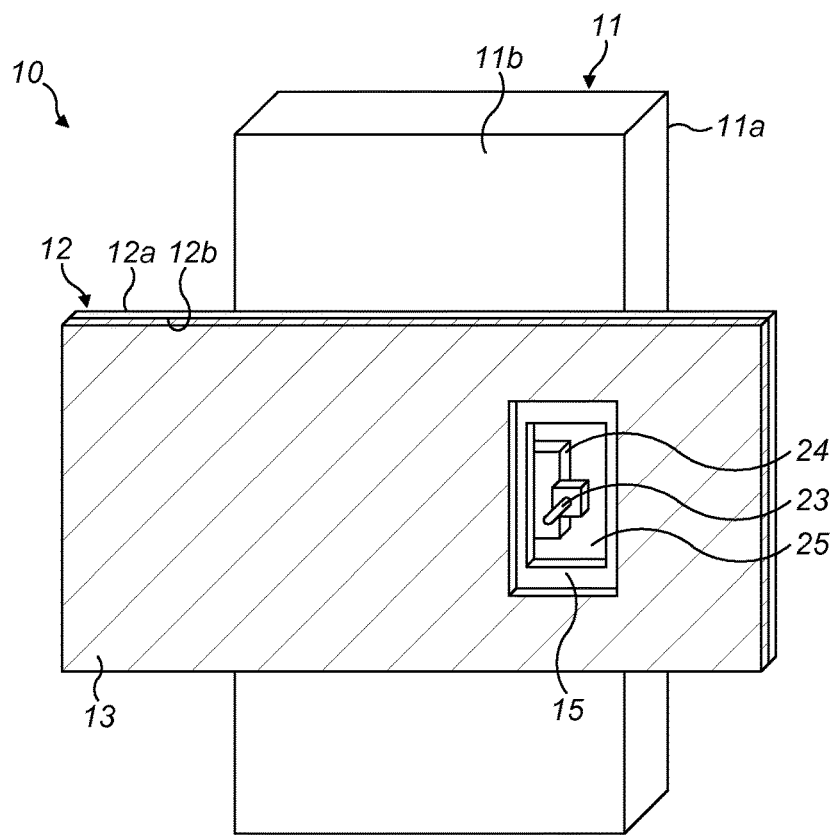
FIG. 3 shows a plan view from below of the medicament delivery device of FIG. 1 in a second position.
Figure 4:
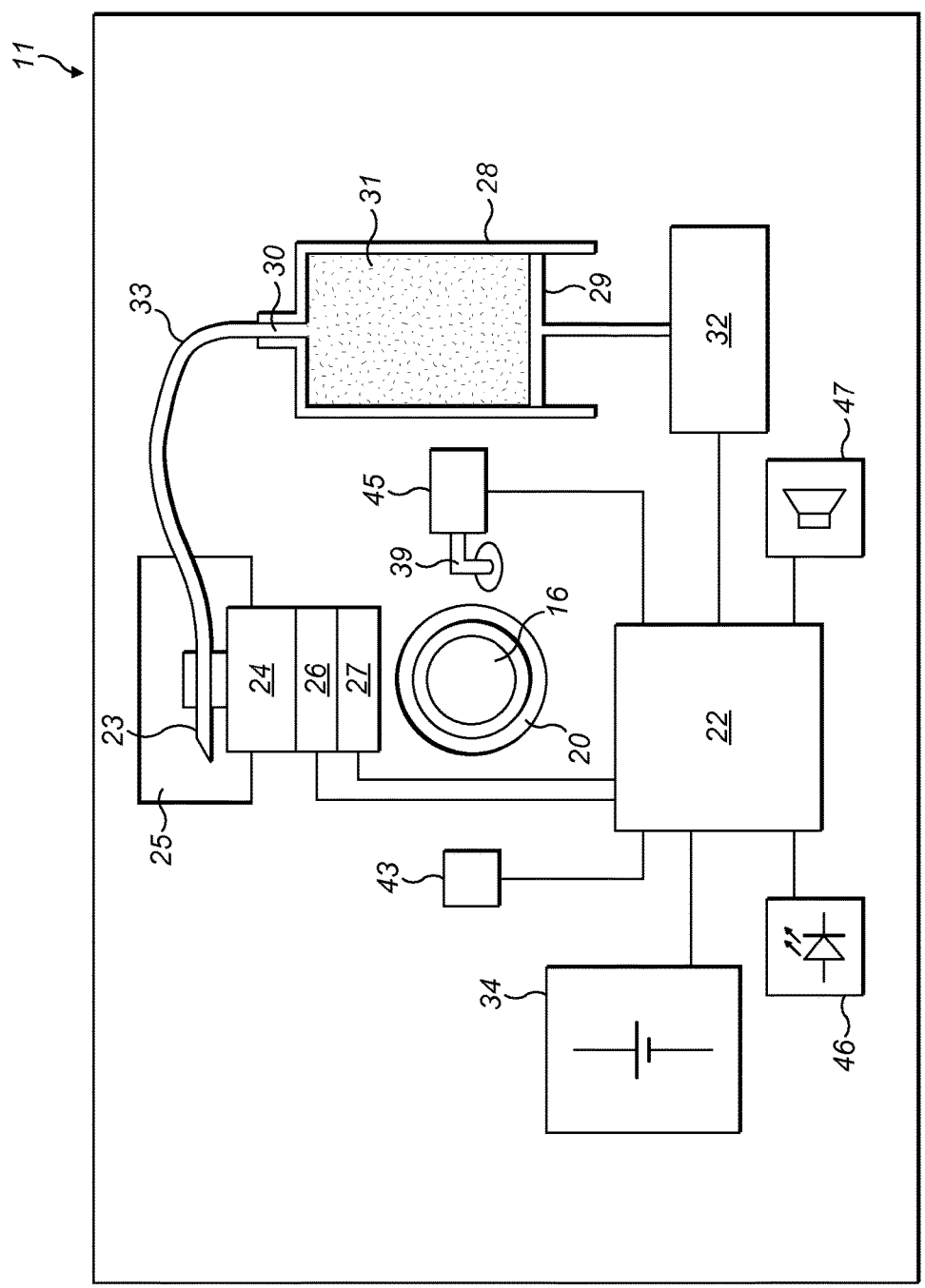
FIG. 4 shows a schematic plan view from above schematically showing the functional components within the housing of the medicament delivery device of FIGS. 1 to 3.

The housing 11 includes an upper side 11a and a lower side 11b. The lower side 11b of the housing 11 includes a needle aperture 25 communicating with the interior cavity of the housing 11. The lower side 11b of the housing 11 also includes a cylindrical recess 17 which extends into the housing 11 and which receives the post 16 of the base plate 12. The housing 11 is thereby rotatable relative to the base plate 12 about the post 16. FIGS. 2 and 3 show the housing 11 in two different positions relative to the base plate 12, and with the cover sheet 14 removed. FIG. 2 shows the housing 11 in a first position which corresponds to an inactive position of the device 10. FIG. 3 shows the housing 11 in a second position which corresponds to an active position of the device 10. The housing 11 is rotatable through approximately 90 degrees relative to the base plate 12 between the first and second positions, although the invention is not intended to be limited to this angular range of movement. It can be seen from FIG. 3 that in the second position of the housing 11, the needle aperture 25 in the housing 11 is aligned with the aperture 15 in the base plate 12.

Figure 5:
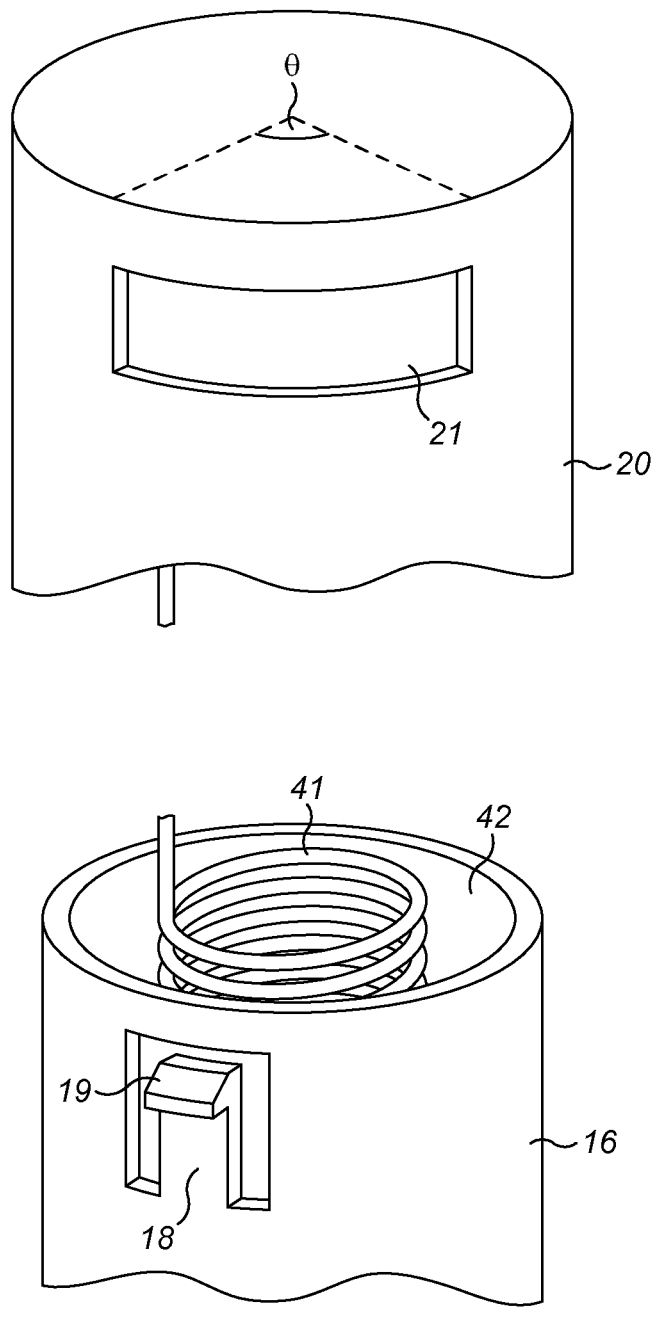
FIG. 5 shows an exploded perspective view of connecting elements of a housing and a base plate of the medicament delivery device of FIGS. 1 to 4.

The housing 11 may be rotatably secured to the base plate 12 by cooperating elements on the post 16 and cylindrical recess 17, as shown in FIG. 5. In this exemplary configuration, the post 16 includes a pair of sprung pawls 18 which include an enlarged head portion 19. A side wall 20 defines the cylindrical recess 17 of the housing 11 and includes a pair of circumferential slots 21 each extending around approximately 90 degrees of the circumference of the side wall 20 on opposite sides thereof, shown by angle θ in FIG. 5. The post 16 is received within the cylindrical recess 17 such that the enlarged heads 19 of the sprung pawls 18 latch into a respective circumferential slot 21. The housing 11 is thereby secured to the base plate 12 and is rotatable relative to the base plate 12. Also, the degree of rotation of the housing 11 relative to the base plate 12 is restricted within a range defined between positions where the enlarged heads 19 of the sprung pawls 18 abut each end of the circumferential slots 21. The desired degree of rotation of the housing 11 relative to the base plate 12 can thereby be pre-determined by the size of the circumferential slots 21 provided in the side wall 20.

The device 10 includes a controller 22 that is configured to control operation of the various components of the device 10. The device 10 includes a needle 23 and a needle insertion mechanism 24. The needle insertion mechanism 24 is controllable by the controller 22 to cause the needle 23 to move between a retracted position and an engaged position. In the retracted position the needle 23 is disposed within the interior cavity of the housing 11, and in the engaged position the needle 23 extends through the needle aperture 25 in the lower side 11b of the housing 11 and thereby projects from the housing 11. When the housing 11 is in the second position relative to the base plate 12, and the needle 23 is in the engaged position, the needle 23 extends through the aperture 15 in the base plate 12 so as to pierce and inject a patient's skin when the device 10 is attached to a patient.

The needle 23 is driven by the needle insertion mechanism 24 to be inserted into the user by a needle driver 26. The needle driver 26 may for instance be an electric motor or a spring release mechanism. In the embodiment in which the needle driver 26 comprises an electric motor, energy for powering the needle driver 26 comes from an energy source 27. However, the form of the energy source 27 corresponds to the form of the needle driver 26, and is discussed below. The needle driver 26 and the energy source 27 are controlled by the controller 22.

A medicament cartridge 28 is provided in the housing 11 which may, for instance, include a vial formed of glass. A plunger 29 is provided within the cartridge 28 at an opposite end to a medicament delivery aperture 30. Between the plunger 29 and the end of the medicament cartridge 28 that includes the medicament delivery aperture 30 is defined a volume that is filled with medicament 31.

A plunger driver 32 is mechanically coupled to the plunger 29. The plunger driver 32 is controllable by the controller 22 to move the plunger 29 along the medicament cartridge 28. When so controlled, the force provided by the plunger 29 on the medicament 31 causes it to be expelled through the medicament delivery aperture 30 and along a medicament delivery tube 33 to the needle 23, in particular, the end of the needle 23 that is opposite to the end that is inserted into the user. When so operated, the medicament 31 is caused to be expelled through the bore of the needle 23.

An electrical power source in the form of a battery 34 is provided. The battery 34 provides electrical power to the controller 22. It may also provide electrical power the plunger driver 32, if this is an electrically driven device. The battery 34 may also constitute the energy source 27, that is to say the energy source 27 and the battery 34 may be combined into a single component.

Figure 6:
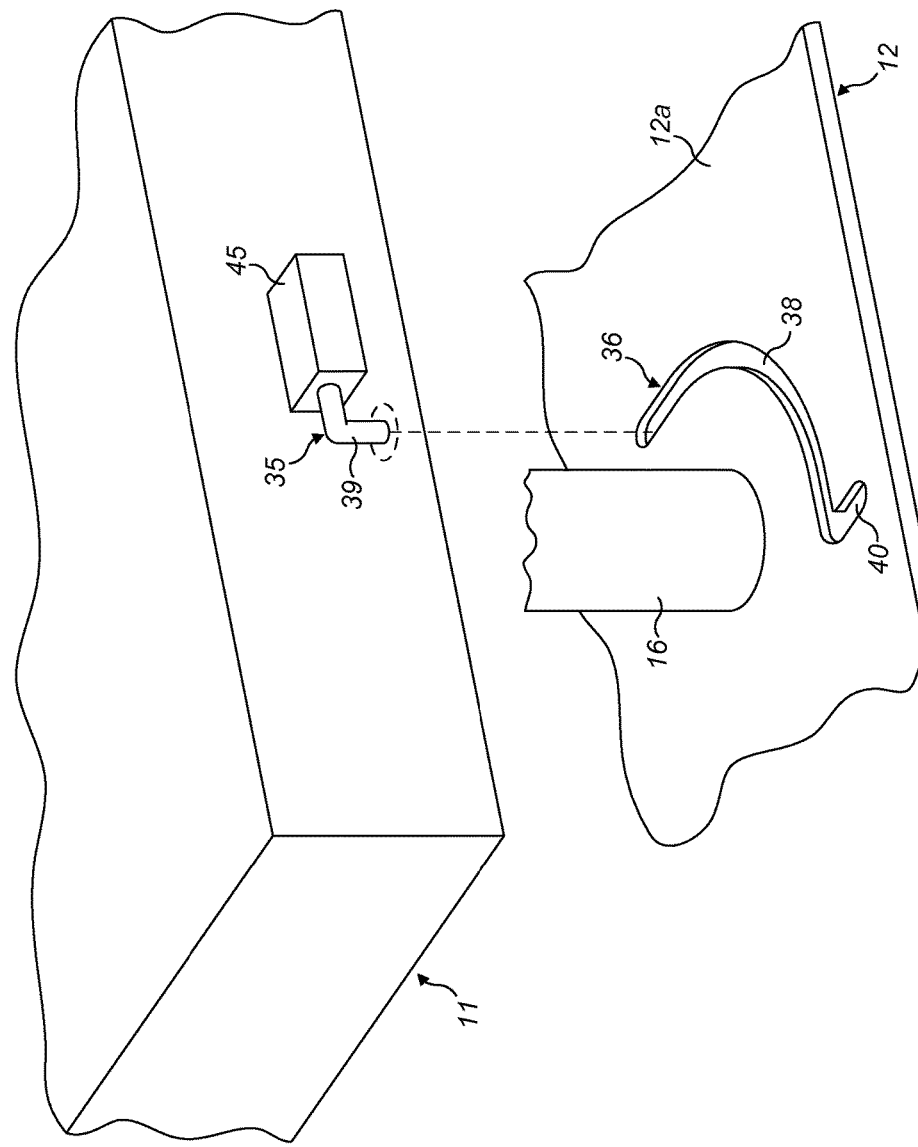
FIG. 6 shows a partial view of cooperating portions of a base plate and housing of the medicament delivery device of FIGS. 1 to 5.

The housing 11 and the base plate 12 respectively comprise cooperating latch members 35, 36 (see FIGS. 1 and 6) which are out of engagement in the first position of the device 10 but come into engagement when the device 10 is manipulated into the second position. Once the latch members 35, 36 are in engagement with each other, the housing 11 is locked in the second position. The housing 11 includes a release button 37 which is coupled to the latch members 35, 36 and is configured such that pressing the button 37 disengages the latch members 35, 36 from each other and thereby allows the housing 11 to be rotated back to the first position. The latch members 35, 36 and button 37 may take any suitable form within the scope of the certain embodiments to achieve the above-described function. For example, one latch member may comprise a recessed guide track 38 formed on the upper surface 12a of the base plate 12 and the other latch member 36 may comprise a sprung follower pin 39 connected to the housing 11 and projecting from the bottom side 11b of the housing 11, and which travels along the guide track 38. The guide 38 may include a detent 40 and the follower pin 39 may be spring-biased to locate into the detent 40 when the device 10 is in the second position. The button 37 may be configured to act upon the follower pin 39 to move it out of the detent 40 to allow relative rotation of the housing 11 and base plate 12. The button 37 may be mechanically coupled to the follower pin 39, or the follower pin 39 may be mounted on a solenoid 45 which is activated to move the follower pin 39 when the button 37 is pressed.

The device 10 may include a spring mechanism which biases the device 10 into the first position. Such a mechanism is shown in FIG. 5 and comprises a spiral spring 41 disposed within a hollow bore 42 of the post 16, and with one end secured to the post, and the other end secured to a portion of the housing 11 within the cylindrical recess 17. When the housing 11 is rotated relative to the base plate 12 from the first position to the second position, the tension in the spiral spring 41 is increased. The spiral spring 41 may be un-tensioned in the first position of the device 10, or may be under a pre-load in the first position of the device 10. The device 10 may include a damping mechanism (not shown) to damp the rotational movement of the housing 11 back to the first position under the biasing force of the spiral spring 41. This may advantageously provide a smoother rotational movement of the housing 11 relative to the base plate 12. Such damping mechanism may comprise, for example, frictional contact between the housing 11 and the base plate 12, such as between the post 16 and the cylindrical recess 17. The frictional contact may be provided by friction pads of suitable material, such as foam, rubber, fabric or felt.

The housing 11 and the base plate 12 respectively comprise cooperating contacts 43, 44 which are out of engagement in the first position of the device 10 but come into contact with each other when the device 10 is rotated into the second position. The housing contact 43 is connected to the controller 22 and the controller is configured to detect when the base plate contact 44 is in contact with the housing contact 43. The controller 22 is configured to prevent operation of the medicament delivery mechanism when the cooperating contacts 43, 44 are out of contact with each other. Therefore, the controller 22 is configured to only permit operation of the medicament delivery mechanism when the device 10 is in the second, active position.

Figure 7:
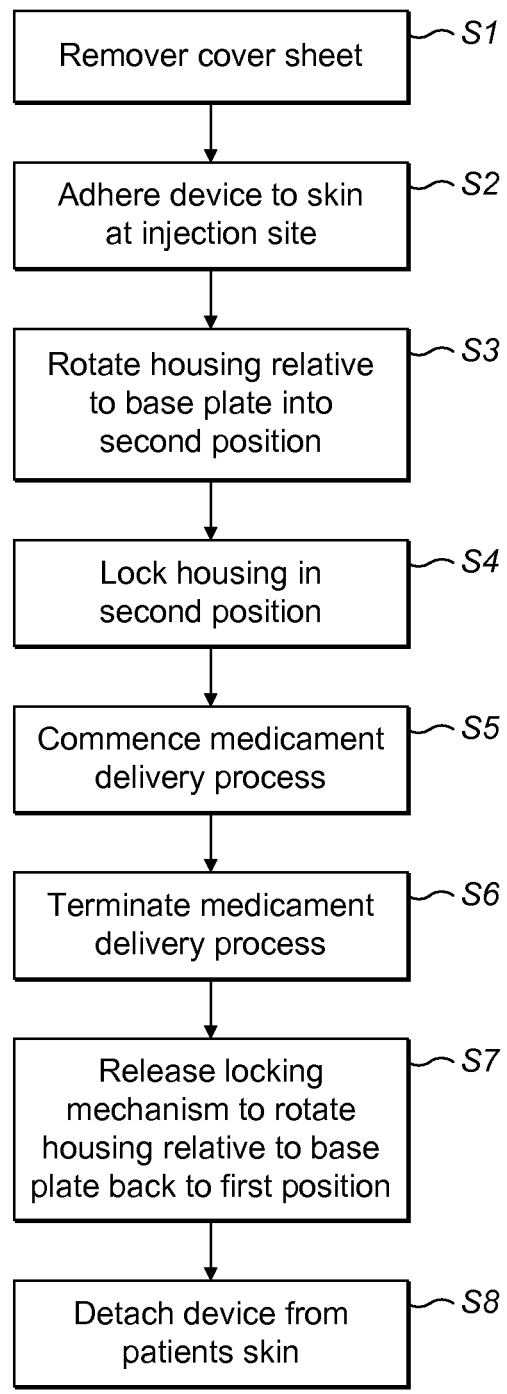
FIG. 7 shows a flow chart of steps of use of the medicament delivery device of FIGS. 1 to 6.

Use of the medicament delivery device 10 of the first embodiment will now be described, with reference to FIG. 7. The method of use will be described in the context of self-administration by a patient, although it is to be understood that the device 10 according to certain embodiments may be operated by a third party on the patient, for example by medical personnel. A patient preferably first prepares an appropriate injection site on their body by sterilization and possibly subsequent drying of the sterilized injection site. The device 10 is provided to the patient in the first position, namely the inactive position shown in FIG. 2. At step S1, a patient removes the cover sheet 14 to expose the adhesive layer 13 and, as step S2, the patient adheres the device 10 to the injection site by pressing the lower surface 12b of the base plate 12 against their skin.

Once the device 10 is securely attached to the patient, as step S3, the patient then grasps the housing 11 and rotates it through 90 degrees relative to the base plate 12, against the force of the spiral spring 41 into the second position, namely the active position shown in FIG. 3. Once in the active position, the housing and base latch members 35, 36 engage to lock the device 10 in the second position at step S4. Also, the housing and base contacts 43, 44 come into contact which is detected by the controller 22. At step S5, the controller 22 then activates the medicament delivery mechanism and the medicament delivery process is commenced. The controller 22 automatically activates the needle driver 25 to move the needle 23 into the engaged position, extending though the needle aperture 25 and the aperture 15 in the base plate 12, to pierce the patient's skin. The controller 22 then activates the plunger driver 32 to move the plunger 29 to deliver medicament 31 to the patient from the cartridge 28. Upon completion of the medicament delivery to the patient, at step S6, the controller 22 stops the plunger driver 32 and activates the needle driver 25 to retract the needle 23 back out of the patient's skin and into the retracted position within the housing. At step S7, the device 10 can be returned to the first position under the biasing force of the tensioned spiral spring 41 by the patient pressing the button 37 to disengage the cooperating latch members 35, 36. Finally, at step S8, the patient can detach the device from their skin. The device 10 can be discarded, in the case of a disposable device, or stored for future use in the case of a reusable device.

It will be appreciated that the device 10 is configured with a number of safety features to prevent a patient accidentally incorrectly operating the device 10 and/or injuring themselves on the needle 23. Firstly, activation of the medicament delivery process by rotating the entire housing 11 relative to the base plate 12, and therefore relative to the patient's body, is a large and deliberate action needed by the patient. The patient is therefore much less likely to accidentally perform this activation movement than if activation was achieved only by pushing a button on the housing, which could accidentally be done by knocking the housing or bumping the housing into another object. Secondly, the needle 23 is inaccessible from outside the device 10 until the device is manipulated into the second position, since in the first position, the needle aperture 25 and the aperture 15 in the base plate 12 are out of alignment. Therefore, a user cannot reach into the device 10 at all to touch the needle 23 when the device is in the first position. Also, even if the needle driver 25 was to malfunction and accidentally attempt to move the needle 23 into the engaged position, it would only abut the upper surface 12a of the base plate 12.

In an optional variant of the first embodiment, the cooperating latch members 35, 36 may be configured to automatically disengage when the medicament delivery process is complete, without the need for a release button 37. This may be activated by an appropriate mechanism, for example a solenoid connected to the controller 22 and mechanically coupled to the cooperating latch members 35, 36. In an embodiment, the solenoid may move the follower pin 39 out of engagement with the detent 40 in the recessed track 38. In such an embodiment, the device 10 would automatically return to the first position upon completion of a medicament delivery, under the biasing force of the spiral spring 41. Alternatively, the latch members 35, 36 may be automatically disengaged by mechanical mechanism, for example a projecting tab (not shown) could extend from the plunger 29. The tab could be configured to engage with the cooperating latch members 35, 36 when the plunger reaches the position at which the medicament 31 has been emptied from the cartridge 28. The tab may act to disengage the cooperating latch members to release the housing 11 so it is free to rotate back to the first position under the force of the spiral spring 41. These arrangements for automatic unlocking of the housing 11 from the second position may be advantageous as the patient would not need to perform any further manipulation of the device 10 after the initial activation step, until the device 10 needs to be removed from their body upon completion of the medicament administration process. In addition, the rotational movement of the housing 11 back to the first position gives the patient a clear and tactile indicator that the medicament delivery process is complete. Such an indicator is also advantageous as it is discrete, for example, it does not include an audible indicator such as a bleep, which can make a patient feel self-conscious or embarrassed if using the device 10 in public.

The device 10 may be configured to detect when a medicament delivery process is complete and take an appropriate action upon said completion. This may include the disengagement of the cooperating latch members 35, 36 as discussed above. Alternatively, or in addition, this may comprise presenting a visual indicator to the patient, and/or producing an audible indicator to the patient. As such, the device 10 may include a light, such as an LED 46 connected to the controller 22, and/or a buzzer 47 or similar noise-generating device, connected to the controller 22. The controller 22 would activate the light 46 and/or buzzer 47 when a medicament delivery process is complete. In order to detect when a medicament delivery process is complete, the device 10 may include a sensor to detect the position of the plunger 29 and so can detect when the plunger 29 has reached a position at which the required dose of medicament 31 has been expelled from the cartridge 28. Alternatively, the controller 22 may actuate the plunger driver 32 for a predetermined period of time and, with stored data on the medicament delivery rate for the medicament delivery mechanism in the controller 22, the controller 22 can ensure a correct dose of medicament is administered to the patient. The controller 22 is then able to determine when the medicament delivery process is complete upon elapse of the relevant predetermined medicament delivery period.

In the device 10 of the first embodiment described above, the needle insertion mechanism 24 is electronically controlled by the controller 22 upon rotation of the housing 11 into the second position. However, the invention is not intended to be limited to this particular configuration and in alternative embodiments, the needle insertion mechanism 24 may be manually actuated in which manual force moves the needle 23 from the retracted position to the engaged position. In such alternative embodiments, the energy source 27 and the needle driver 26 may be omitted, and the needle driver 26 may be substituted with a mechanism for communicating user-applied work to movement of the needle 23 via the needle insertion mechanism 24. The communicating mechanism may translate patient-provided work in the form of a rotational movement or a slide movement or a depression movement into movement of the needle 23 to be inserted into the tissue of the patient. In one such alternative embodiment, the needle insertion mechanism 24 may be mechanically coupled to the housing 11 and the base plate 12 such that rotation of the housing 11 from the first position to the second position causes the needle 23 to move from the retracted position to the engaged position. The communication mechanism may comprise a cam surface on one of the housing 11 and the base plate 12, and a cam follower on the other of the housing 11 and the base plate 12. The cam follower may cooperate with the needle insertion mechanism 24 to move the needle 23 into the engaged position as the housing 11 is rotated relative to the base plate 12 into the second position. The needle 23 may be biased into the retracted position so that upon movement of the device 10 back to the first position, the needle 23 moves back to the retracted position under the biasing force.

The invention is not intended to be limited to devices in which the needle 23 is mounted within the housing 11 and may include embodiments in which the needle 23, and/or the needle insertion mechanism may be mounted on the base plate 12. In such embodiments, the cartridge 28, plunger 29 and plunger driver may be contained within the housing 11 and connected to the needle 23 via the medicament delivery tube 22 which is of sufficient length and flexibility to allow for relative movement between the needle 23 and cartridge 28 as the device is moved between the first and second positions. It will also be appreciated that in such embodiments, the lower side 11b of the housing 11 may include a sufficiently large aperture to accommodate the needle 23 and needle insertion mechanism 24 between both the first and second positions of the device 10. In such embodiments, the needle 23 would be movable between an engaged position in which the needle 23 extends through the aperture 15 in the base plate 12 to pierce a patient's skin, to a retracted position in which the needle 23 does not extend through the aperture 15 in the base plate 12, but may not necessarily be disposed within the interior cavity of the housing 12.

An embodiment in which the needle 23 and needle insertion mechanism 24 may be mounted to the base plate 12, may also include the communicating mechanism described above, to translate patient-provided work into movement of the needle 23. Such an embodiment may include a cam surface provided on one of the housing 11 and the needle 23/needle insertion mechanism 24, and a cam follower provided on the other of the housing 11 and the needle 23/needle insertion mechanism 24.

The invention is not intended to be limited to devices in which the needle 23 is moveably mounted within the housing 11 or on the base plate 12. In certain aspects, devices in which the needle 23 is fixed and extends beyond the base plate 12 are provided. In such embodiments, the needle may permanently extend though the aperture 15 in the base plate 12. In such embodiments, movement of the housing from the first position to the second position would not be linked to any needle movement, but would be linked to activation of the device and/or commencement of a medicament delivery function.

The invention is not intended to be limited to devices in which the needle 23 extends through an is mounted within the housing 11. In some embodiments the needle 23 may be located outside an outer perimeter edge of the base plate 12.

In a further embodiment, once the housing 11 is rotated relative to the base plate 12 into the second position, the housing 11 may slowly rotate back to the first position during the medicament delivery process, and arrive back in the first position once the medicament delivery process is complete. It will be appreciated that in such an embodiment, the needle 23 would need to be mounted on the base plate 12 as the needle 23 would need to remain in a fixed position inserted in the patient's skin during the medicament delivery process. In such an embodiment, the device 10 may include an appropriate rotational mechanism coupling the housing 11 to the base plate 12 to allow the housing to rotate back to the first position over a predetermined time period of medicament delivery. Such a rotational mechanism may include a spring and friction element to allow a slow release of the housing 11 back to the first position. Alternatively, the rotational mechanism may comprise an electric motor and a gear arrangement. For example, the motor may drive a worm gear which is in engagement with a spur gear to slowly rotate the housing 11 back to the first position. In such an embodiment, the motor and worm gear may be mounted to one of the housing 11 and the base plate 12, and the spur gear may be mounted to the other of the housing 11 and the base plate 12. Such embodiments may be advantageous as they may provide a subtle and clear indicator to the patient when the medicament delivery process is complete, that is when the device 10 has returned back to the first position, without necessarily requiring a visual or audible indicator. Also, the relative position of the housing 11 and the base plate 12 can give the patient an indication as to the progress of the medicament delivery process. For example, if the housing is at a position of 45 degrees relative to the base plate 12, the patient can see that the medicament process is halfway complete (if the housing 11 is moved relative to the base plate 12 by 90 degrees between the first and second positions, and the return movement back to the first position is at a constant speed).

The invention is not intended to be limited to devices in which the housing 11 is rotatable relative to the base plate 12 and the housing may be moveable relative to the base plate between the first and second positions in other ranges of motion, for example by translational or sliding movement. In such embodiments, cooperating sliding members may be provided between the housing 11 and the base plate 12. Such sliding members may comprise, for example, interlocking sliding rails.

The invention is not intended to be limited to devices in which the housing 11 is rotationally biased relative to the base plate 12, for example, by the spiral spring 41. Alternative biasing elements are intended within the scope of some embodiments, for example, but not limited to, torsion spring, leaf spring, an elastic member, or fluid-operated piston. Furthermore, the spiral spring 41 or other biasing element may be omitted and the housing 11 may be manually manipulated between the first and second positions.

The invention is not intended to be limited to devices in which relative movement between the housing 11 and the base plate 12 is restricted between the first and second positions. The housing may be moveable beyond the second position by a certain distance or degree. This may advantageously allow a patient to be sure the device has been fully moved into the second position for successful operation of the device. For example, the patient may be able to move the housing beyond the second position and then move the housing back to the second position. The device may include a catch or locking means to prevent the housing moving back to the first position, but to allow the housing to be moved beyond the second position. A user may thereby move the housing beyond the second position and back to the second position, at which point the catch or locking means would hold the housing in the second position. The device may include a spring or other biasing means to urge the housing back to the second position if moved beyond the second position. The device may include a sensory indicator which indicates to a patient when the device has reached the second position. For example, inter-engaging elements between the housing and the base plate 12 may create an indicator, such as a click or other audible indicator, when the housing reaches the second position. The device may include cooperating elements to prevent the housing being moved more than a predetermined distance or degree beyond the second position. For example, stop elements may be provided between the housing and base plate that abut when the housing reaches a predetermined distance or degree beyond the second position.

The invention is not intended to be limited to devices in which relative rotational movement between the housing 11 and the base plate 12 is restricted to a certain angle of rotation such as 90 degrees as described above, and the housing may be rotatable relative to the base plate through any angle between the first and second positions. Ninety degrees may be preferable from a usability perspective as it is a comfortable angle of rotation for a patient's wrist. However, 180 may be preferable since, due to the rectangular shape of the housing and base plate, the housing would be visibly realigned with the shape of the base plate and would therefore give a patient an indicator that the housing had been properly and fully moved into the second position. The housing may be rotatable through more than 180 degrees or more than 360 degrees.

The invention is not intended to be limited to devices in which the device is adhered to a patient before the housing or moved relative to the base plate 12. The device may equally be moveable into the second position prior to securing the device to the patient's body.

In the embodiments described above, the device 10 is configured such that the needle 23 extends into the patient's skin substantially perpendicularly to the base plate 12 and thereby to the surface of the patient's skin. This may advantageously enable a required depth of injection to be achieve with a minimal needle length and/or distance of needle movement. It may also advantageously reduce stress on the needle during insertion. However, the invention is not intended to be limited to such a configuration, and the device may be configured to inject the needle at an angle less than perpendicular to the base plate 12 and thereby the patient's skin. Such alternative embodiments may be advantageous as they could enable a certain depth of injection to be more accurately achieved. That is, a greater movement in the direction of the needle length is required for a given depth of injection into the patient's skin. Therefore, less fine control over the distance of needle movement may be required.

Devices intended within the scope of the certain embodiments may comprise a medicament delivery mechanism driver to at least partially power the medicament delivery mechanism. For example, a medicament delivery mechanism driver may power a needle insertion mechanism to inject the needle into a patient and/or a mechanism to expel medicament from a reservoir into a patient via the needle 23 if a hollow needle, or via a cannula inserted into the patient by means of a solid needle. For example, the energy may drive a plunger within a medicament reservoir cartridge. Energy may be provided to the medicament delivery mechanism driver by movement of the housing into the second position. For example, the medicament delivery mechanism driver may comprise a spring that is compressed, wound up or otherwise energized when the housing is moved into the second position. In such a case, work done by the patient is converted into stored energy in the spring. Release of this energy by may power the device. Alternatively, the medicament delivery mechanism may be electrically powered. For example, the medicament delivery mechanism driver may include an electricity generation unit configured to convert work done by the patient in moving the housing into the second position into stored electrical energy in, for example, a battery or capacitor. The housing may be rotatable through any range of motion to power the medicament delivery mechanism driver, and may be rotatable through more than one complete revolution.

In the embodiments described above, the device 10 is configured to automatically commence a medicament delivery process once the device is manipulated into the second position. However, the invention is not intended to be limited to such a configuration and the device may be configured to activate or "prime" the medicament delivery mechanism ready for a medicament process to be commenced, but a further actuation by a patient may be required to commence the medicament delivery process. For example, the device may include a start button which a user must depress to initiate the medicament delivery process once the device has been moved into the second position. The needle insertion mechanism 24 may still be automatically actuated when the device 10 is moved into the second position so that the needle 23 pierces the patient's skin, and the start button may be pressed to activate the plunger driver 32 to commence medicament delivery. Alternatively, the needle insertion mechanism 24 may not be activated until the start button is pressed in addition to movement of the device 10 into the second position. It will be appreciated that in such alternative embodiments, the device 10 may still provide the advantage of avoiding accidental operation of the device, as the rotation of the housing 11 relative to the base plate 12 is still required before medicament delivery can be commenced and so simply accidentally pressing the start button while the device 10 is in the first position would not begin operation of the device 10. Activation of the device 10 by moving the device 10 into the second position may be achieved by only conducting power from the battery 34 when the device 10 is in the second position, for example by providing an electrical connection which is only made when the device is in the second position. Alternatively, the device 10 may include a sensor coupled to the controller 22 and configured to detect relative positions of the housing 11 and base plate 12, and the controller 22 may be programmed only to allow operation of the device 10 in the second position.

The invention is not intended to be limited to devices in which the base plate 12 is substantially planar, and embodiments may include non-planar and curved base plates 12. A non-planar base plate 12 may be advantageous as it could be configured to conform to the contours of a patient's body to which the device 10 is intended to be attached, such as the thigh or torso.

The base plate 12 may be a solid or flexible component within the scope of the certain embodiments, and may be made of any suitable material, including plastic, fabric, textile or rubber, or may be made of a combination of materials. In addition, the base plate may comprise a frame over which a web of material is provided, for example a plastic frame with a fabric web provided over the frame.

The invention is not intended to be limited to devices which are secured to a patient's body by adhesive. In alternative embodiments, the device may be provided with a belt or strap to secure the base plate 12 to the patient's body. Alternatively, a base plate may define a cavity in its lower surface 12b which is fluidly coupled to a source of vacuum to retain the device on the patient's body by suction.

Although the liquid medicament 31 is shown as being provided in a cartridge 28 within the housing 11, the invention is not limited to this configuration and in an alternative embodiment (not shown), the liquid medicament may be provided externally of the device 10 in a remote reservoir. Furthermore, the invention is not intended to be limited to devices in which the medicament is contained within the device in a cartridge, and certain embodiments can encompass any other configuration of medicament reservoir, which may be rigid or flexible, for example, a pouch of medicament.

It will be appreciated that the medicament delivery devices of certain embodiments may be applicable to LVDs. However, the invention is not intended to be limited to this particular type of medicament delivery device and embodiments can include alternative types of medicament delivery devices which function in contact with a patient's skin, such as, for example, patch pumps and infusion pumps.

The medicament delivery device according to certain embodiments includes a needle 23 to pierce a patient's skin as part of the process of injecting a medicament through a patient's skin into their body. Such devices include, for example, patch pumps and infusion devices in which the medicament is delivered into the patient's tissue. The embodiments are particularly suited to bolus injections, but the injection device may instead be of the basal type.

Devices intended to fall within the scope of certain embodiments may include a hollow needle through which the medicament is delivered, or a solid needle, such as in trocar devices, in which a solid needle or obturator pierces the skin and a hollow tube or cannula is subsequently inserted into the pierced hole and through which the medicament is subsequently delivered to the patient. In trocar devices, the solid needle or obturator does not remain in the patient's skin during medicament delivery.

The medicament delivery mechanism may take any suitable form. It may for instance include an electric motor and a gear mechanism that causes insertion of the needle 23 into the user. It may alternatively be a mechanical spring based mechanism. In this case the needle 23 driving energy source is a preloaded spring, and a needle insertion mechanism driver may be a spring release mechanism that causes force from the spring to be communicated to a needle insertion mechanism thereby to insert the needle 23 into the patient.

In the exemplary method of use of the device 10 of an embodiment described above, the housing 11 is rotated back to the first position upon completion of the medicament delivery process and before the device 10 is detached from the patent. However, the invention is not intended to be limited to such configuration of device 10 and method of use, and in alternative embodiments, the housing 11 may remain in the second position at the end of a medicament delivery process. In such an embodiment, the device may still include a locking mechanism to lock the housing 11 in the second position relative to the base plate 12, although a release mechanism to disengage the locking mechanism may not necessarily be required.

An insertion mechanism for inserting the needle may take any suitable form. It may be a mechanical spring based mechanism. Alternatively, the insertion element mechanism may for instance include an electric motor and a gear mechanism that causes insertion of the insertion element into the user. In alternative embodiments, a needle insertion mechanism driver may be a gas or fluid pressure operated mechanism, in which case the needle driving energy source is either a reservoir of pressurised gas or a chemical system in which two or more chemicals are mixed together to produce gas or fluid pressure.

It will be appreciated that the embodiments shown in the figures are illustrated schematically for clarity and ease of illustration of certain aspects, and the dimensions and proportions are not accurate. For example, the thicknesses of the adhesive layer and cover sheet are exaggerated.

The devices of certain embodiments are configured to deliver the medicament subcutaneously, although may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, σ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and σ approximately 500 amino acids, while μ and ε have approximately 550 amino acids.

Each heavy chain has two regions, the constant region (CH) and the variable region (VH). In one species, the constant region is essentially identical in all antibodies of the same isotype, but differs in antibodies of different isotypes. Heavy chains γ, α and σ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula. Initially, both the trocar and cannula may move together to pierce the skin. The trocar may then retract while the cannula remains at least partially within the target tissue. Later, the cannula may separately retract into the delivery device.

The invention claimed is:

1. A medicament delivery device comprising:
   a medicament delivery mechanism including an injection needle;
   a housing containing the medicament delivery mechanism; and
   a base plate with a contact surface for placement against a body of a patient;
   wherein the housing includes a lower side that is rotatably connected to the base plate, by a rotational mechanism, about an axis substantially perpendicular to the plane of the contact surface of the base plate such that the housing is rotatable relative to the base plate between a first position and a second position;
   wherein the medicament delivery mechanism is operative upon movement of the housing from the first position to the second position; and
   wherein the rotational mechanism is configured to:
      rotate the housing to the second position; and
      rotate, after a medicament delivery process is initiated and once the housing has been rotated into the second position, the housing back toward the first position over a predefined period of the medicament delivery process.

2. The medicament delivery device according to claim 1, wherein the base plate includes an aperture through which the injection needle is able to extend.

3. The medicament delivery device according to claim 1, wherein the medicament delivery mechanism is configured to automatically initiate a medicament delivery process when the housing is moved into the second position.

4. The medicament delivery device according to claim 1, wherein:
   the medicament delivery mechanism is activated when the housing is moved into the second position, and
   the medicament delivery device includes an actuator manually operable to initiate a medicament delivery process when the housing is moved into the second position.

5. The medicament delivery device according to claim 1, wherein the injection needle is moveable between an engaged position in which it projects outwardly beyond the contact surface of the base plate and a retracted position.

6. The medicament delivery device according to claim 5, wherein the medicament delivery mechanism comprises a needle insertion mechanism configured to automatically move the injection needle into the engaged position when the housing is moved into the second position.

7. The medicament delivery device according to claim 1, further comprising a biasing element configured to urge the housing into the first position.

8. The medicament delivery device according to claim 1, wherein the medicament delivery mechanism is at least partially powered by a medicament delivery mechanism driver configured to be energized when the housing is moved to the second position.

9. The medicament delivery device according to claim 1, comprising a locking mechanism configured to lock the housing in the second position relative to the base plate, and a release mechanism configured to release the housing from the second position relative to the base plate.

10. The medicament delivery device according to claim 9, wherein the release mechanism is configured to automatically release the locking mechanism.

11. The medicament delivery device according to claim 1, wherein the housing is rotatable about a limited range of rotation relative to the base plate, ends of the limited range of rotation being defined by the first position and the second position.

12. The medicament delivery device according to claim 1, wherein the housing is moveable relative to the base plate beyond the second position from the first position, and moveable back to the second position for operation of the medicament delivery mechanism.

13. A method of delivering medicament to a patient using a medicament delivery device, the medicament delivery device comprising:
   a medicament delivery mechanism including an injection needle;
   a housing containing the medicament delivery mechanism; and
   a base plate with a contact surface for placement against a body of a patient;
   wherein the housing includes a lower side that is rotatably connected to the base plate, by a rotational mechanism, about an axis substantially perpendicular to the plane of the contact surface of the base plate such that the housing is rotatable relative to the base plate between a first position and a second position;
   wherein the medicament delivery mechanism is operative upon movement of the housing from the first position to the second position; and
   wherein the rotational mechanism is configured to:
      rotate the housing to the second position; and
      rotate, after a medicament delivery process is initiated and once the housing has been rotated into the second position, the housing back toward the first position over a predefined period of the medicament delivery process;
the method comprising:
   detecting, by a controller, movement of the housing of the medicament delivery device from the first position to the second position relative to an injection site on the patient;
   activating, by the controller, the medicament delivery mechanism of the medicament delivery device in response to detecting the movement of the housing; and
   initiating a medicament delivery process in which the medicament delivery mechanism is operated to deliver medicament through the injection site to the patient.

14. The method according to claim 13, wherein, during the medicament delivery process, the medicament delivery mechanism is operated to:
   move the injection needle of the medicament delivery device to pierce the injection site of the patient,
   move a plunger to deliver the medicament from the medicament delivery device to the patient, and
   retract the needle of the medicament delivery device into the housing of the medicament delivery device.

* * * * *

UNITED STATES PATENT AND TRADEMARK OFFICE
CERTIFICATE OF CORRECTION

PATENT NO. : 10,485,925 B2  
APPLICATION NO. : 15/510400  
DATED : November 26, 2019  
INVENTOR(S) : Eva Schiendzielorz and Stefan Wendland Page 1 of 1

It is certified that error appears in the above-identified patent and that said Letters Patent is hereby corrected as shown below:

On the Title Page

Column 2, Lines 1-10, under "ABSTRACT", delete "A medicament delivery device (10) comprises a medicament delivery mechanism including an injection needle (23). A housing (11) contains at least one component of the medicament delivery mechanism. A base plate (12) includes a contact surface (12b) for placement against a patient's body. The housing (11) is moveably connected to the base plate (12) and is moveable relative to the base plate (12) between a first position and a second position. The medicament delivery mechanism is operative upon movement of the housing (11) from the first position to the second position."

And insert -- A medicament delivery device includes a medicament delivery mechanism including an injection needle. A housing contains at least one component of the medicament delivery mechanism. A base plate includes a contact surface for placement against a patient's body. The housing is moveably connected to the base plate and is moveable relative to the base plate between a first position and a second position. The medicament delivery mechanism is operative upon movement of the housing from the first position to the second position. --

Signed and Sealed this  
Eighteenth Day of February, 2020

Andrei Iancu  
*Director of the United States Patent and Trademark Office*